US008877930B2

(12) United States Patent
Bedore et al.

(10) Patent No.: US 8,877,930 B2
(45) Date of Patent: Nov. 4, 2014

(54) CONTINUOUS FLOW SYNTHESIS OF AMINO ALCOHOLS USING MICROREACTORS

(75) Inventors: Matthew W. Bedore, Portage, MI (US); Nikolay Zaborenko, Indianapolis, IN (US); Klavs F. Jensen, Lexington, MA (US); Timothy F. Jamison, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 520 days.

(21) Appl. No.: 12/939,516

(22) Filed: Nov. 4, 2010

(65) Prior Publication Data
US 2011/0118469 A1 May 19, 2011

Related U.S. Application Data

(60) Provisional application No. 61/258,140, filed on Nov. 4, 2009.

(51) Int. Cl.
*C07D 215/26* (2006.01)
*C07D 209/08* (2006.01)
*C07C 213/04* (2006.01)
*B01J 19/00* (2006.01)

(52) U.S. Cl.
CPC ............ *C07C 213/04* (2013.01); *C07D 209/08* (2013.01); *B01J 2219/00891* (2013.01); *B01J 2219/00788* (2013.01); *B01J 2219/00952* (2013.01); *B01J 2219/00828* (2013.01); *C07C 2102/08* (2013.01); *B01J 2219/00873* (2013.01); *C07D 215/26* (2013.01); *B01J 2219/00889* (2013.01); *B01J 19/0093* (2013.01); *C07C 2101/14* (2013.01); *B01J 2219/0081* (2013.01)
USPC ........................................................ 546/153

(58) Field of Classification Search
CPC ............................ C07D 215/26; C07D 209/08
USPC .......................................... 514/312; 546/153
See application file for complete search history.

(56) References Cited

U.S. PATENT DOCUMENTS

| 3,960,973 | A | 6/1976 | Stapp | |
|---|---|---|---|---|
| 4,126,751 | A | 11/1978 | Stapp | |
| 6,252,113 | B1 | 6/2001 | Palmer et al. | |
| 6,645,432 | B1 | 11/2003 | Anderson et al. | |
| 6,878,721 | B1 * | 4/2005 | Cuenoud et al. | 514/312 |
| 7,622,483 | B2 * | 11/2009 | Cuenoud et al. | 514/312 |
| 7,820,694 | B2 * | 10/2010 | Cuenoud et al. | 514/312 |
| 8,067,437 | B2 * | 11/2011 | Cuenoud et al. | 514/312 |
| 8,283,362 | B2 * | 10/2012 | Cuenoud et al. | 514/312 |
| 8,314,246 | B2 | 11/2012 | Jamison et al. | |
| 8,389,551 | B2 * | 3/2013 | Datla et al. | 514/352 |
| 2005/0107635 | A1 | 5/2005 | Mehra et al. | |
| 2005/0245628 | A1 | 11/2005 | Hubel et al. | |
| 2007/0073068 | A1 | 3/2007 | Quaedflieg et al. | |
| 2007/0197801 | A1 | 8/2007 | Bolk et al. | |
| 2011/0118469 | A1 | 5/2011 | Bedore et al. | |
| 2011/0257415 | A1 | 10/2011 | Jamison et al. | |

FOREIGN PATENT DOCUMENTS

| IN | 177748 A1 | 2/1997 |
|---|---|---|
| WO | WO 95/25104 A1 | 9/1995 |
| WO | WO 98/22426 A1 | 5/1998 |
| WO | WO 00/75114 A1 | 12/2000 |
| WO | WO 2004/076422 A1 | 9/2004 |
| WO | WO 2005/037819 A1 | 4/2005 |
| WO | WO 2005/123684 A2 | 12/2005 |
| WO | WO 2006/023457 A1 | 3/2006 |
| WO | WO 2007/141593 A2 | 12/2007 |
| WO | WO 2008/028586 A1 | 3/2008 |
| WO | WO 2008/068927 A1 | 6/2008 |

OTHER PUBLICATIONS

Srinivas, Catal Sury Asia, vol. 12, pp. 114-130, 2008.*
Koch, Biotechnology & Bioengineering, vol. 99, No. 4, Mar. 1, 2008, pp. 1028-1033.*
Sugimoto, Tetrahedron Lett, vol. 47, pp. 6197-6200, 2006.*
Yamashita, Chem Phys Chem, vol. 8, pp. 1307-1310, 2007.*
International Search Report and Written Opinion for PCT/US2006/033829 mailed Feb. 1, 2007.
International Preliminary Report on Patentability for PCT/US2006/033829 mailed Mar. 4, 2008.
International Search Report and Written Opinion for PCT/US2010/055386 mailed Mar. 23, 2011.
International Preliminary Report on Patentability for PCT/US2010/055386 mailed May 18, 2012.
Invitation to Pay Additional Fees for PCT/US2011/026439 mailed Apr. 28, 2011.
International Search Report and Written Opinion for PCT/US2011/026439 mailed Jul. 11, 2011.
International Preliminary Report on Patentability for PCT/US2011/026439 mailed Sep. 13, 2012.
[No Author Listed] Microreactiors find new niches. Chemical Engineering, Access Intelligence Association, Rockville, MA. Mar. 1997 1:30-1,33.
Adams et al., "The Prins Reaction," Synthesis 1977, 661-672.
Ager et al., An Epoxidation Approach to a Chiral Lactone: Application of the Shi Epoxidation. J Org Proc Rev Dev. 2007;11:44-51.
Anderson et al., The preparation of β-substituted amines from mixtures of epoxide opening products via a common aziridinium ion intermediate. Tetrahedron: Asymmetry 1999, 10, 2655-63.

(Continued)

*Primary Examiner* — D M Seaman
(74) *Attorney, Agent, or Firm* — Wolf, Greenfield & Sacks, P.C.

(57) ABSTRACT

The present invention provides various methods for the synthesis of chemical species in a microreactor environment. In some cases, reaction products of the present invention may be valuable as intermediates and/or products in pharmaceutical and polymer research. For example, the method may involve the synthesis of amino alcohols within a microchannel. Embodiment described herein may allow for reactions with significantly shorter reaction times and increased efficiency.

28 Claims, 5 Drawing Sheets

(56) References Cited

OTHER PUBLICATIONS

Arundale, E. et. al., "The Olefin-Aldehyde Condensation: The Prins Reaction," *Chem. Rev.* 1953, 52, 505-555.

Azizi et al., Highly Chemoselective Addition of Amines to Epoxides in Water. *Org. Lett.* 2005, 7,3649-51.

Bach et al., Photochemical deconjugation of chiral 3-methyl-2-butenoates derived from carbohydrate-based alcohols: the influence of the sugar backbone on the facial diastereoselectivity. J Org Chem. May 18, 2001;66(10):3427-34.

Bedore et al., Aminolysis of Epoxides in a Microreactor system: a continuous flow approach to β-Amino alcohols. Org Process Res Dev. 2010;14(2):432-40.

Beessieres et al., Iodomethyl group as a hydroxymethyl synthetic equivalent: application to the syntheses of D-manno-hept-2-ulose and 1-fructose derivatives. J Org Chem. May 16, 2003;68(10):4100-3.

Benito-Lopez et al., High pressure in organic chemistry on the way to miniaturization. *Tetrahedron* 2008, 64, 10023-40.

Bergmeier, The Synthesis of Vicinal Amino Alcohols. Tetrahedron 2000, 56, 2561-76.

Bonollo et al., A green route to β-amino alcohols via the uncatalyzed aminolysis of 1,2-epoxides by alkyl- and arylamines. *Green Chem.* 2006, 8,960-4.

Bowman et al., Approaches for Scale-Up of Microwave-Promoted Reactions. A. *Org. Process Res. Dev.* 2008, 12,41-57.

Bowman et al., Scale-Up of Microwave-Promoted Reactions to the Multigram Level Using a Sealed-Vessel Microwave Apparatus. *Org. Process Res. Dev.* 2008, 12,1078-88.

Brady JR, Cyclic acetals of ketoses ☆: Part III. Re-investigation of the synthesis of the isomeric DI-O-isopropylidene-β-d-fructopyranoses. Carbohydro Res. 1970;15:35-40.

Brandsma et al., "The first successful direct metallation of ethene," J. Chem. Soc., Chem. Comm 1986, 260-1.

Budnik et al., Epoxidation of olefins with molecular oxygen in the presence of cobalt complexes. J Org Chem. 1976;41:1386. (Numbers or something was off).

Cepanec et al., Calcium trifluoromethanesulfonate-catalysed aminolysis of epoxides. Tetrahedron, 2003, 59, 2435.

Chini et al., Lanthanide(III) trifluoromethanesulfonates as extraordinarily effective new catalysts for the aminolysis of 1,2-epoxides *Tetrahedron Lett.* 1994, 35, 433.

Córdova et al., Direct organocatalytic aldol reactions in buffered aqueous media. Chem Commun (Camb). Dec. 21, 2002;(24):3024-5.

Cossy et al., Regioselective ring opening of epoxides by nucleophiles mediated by lithium bistrifluoromethanesulfonimide. *Tetrahedron Lett.* 2002,43,7083.

Couturier et al., Efficient synthesis of the κ-opioid receptor agonist CJ-15,161: four stereospecific inversions at a single aziridinium stereogenic center. Tetrahedron Asymmetry. Nov. 14, 2003;14(22):3517-23.

Crowe et al., "Titanium-Catalyzed Reductive Cyclization of d,e-Unsaturated Ketones and Aldehydes," *J. Am. Chem. Soc.* 1995, 117, 6787-8.

Desai et al., Regioselectivity in a Highly Efficient, Microwave-Assisted Epoxide Aminolysis. *Synthesis* 2007, 902.

Enders et al., Direct organocatalytic de novo synthesis of carbohydrates. Ang Chem Int Ed. 2005;44:1210.

Fayet et al., Synthesis of 3-substituted furans from 3-C-substituted hexuloses. Carbohydro Res. Nov. 1, 1986 1;155:99-106.

Glasnov et al., Microwave-Assisted Synthesis under Continuous-Flow Conditions. *Macromol. Rapid Commun.* 2007,28,395-410.

Goodell et al., Development of an Automated Microfluidic Reaction Platform for Multidimensional Screening: Reaction Discovery Employing Bicyclo[3.2.1]octanoid Scaffolds. J. Org. Chem. 2009;74(16):6169-80.

Hayashi, M., "Fluoride-catalyzed three-component coupling reaction of a silylphosphine, activated alkenes and aldehydes," *Tet Lett.* 2005, 46, 5135-5138.

Ho et al., Nickel-catalyzed, carbonyl-ene-type reactions: selective for aplha olefins and more efficient with electron-rich aldehydes. J Am Chem Soc. 2006;128:5632-3.

Huang et al., "Highly Selective Catalytic Intermolecular Reductive Coupling of Alkynes and Aldehydes," *Org. Lett. 2000*, 2, 4221-4223.

Jang et al., "Hydrogen-Mediated C-C Bond Formation: Catalytic Regio- and Stereoselective Reductive Condensation of α-Keto Aldehydes and 1,3-Enynes," *J. Am. Chem. Soc.* 2004, 126, 4664-4668.

Jang et al., "Reductive Generation of Enolates from Enones Using Elemental Hydrogen: Catalytic C-C Bond Formation under Hydrogenative Conditions," *J. Am. Chem. Soc.* 2002, 124, 15156-15157.

Jang et al., A New catalytic C[bond]C bond-forming hydrogenation: reductive coupling of dienes and glyoxals under catalytic hydrogenation conditions. *Angew. Chem. Int. Ed.* 2003, 42, 4074-4077.

Jas et al., Continuous Flow Techniques in Organic Synthesis. *Chem. Eur. J.* 2003, 9, 5708-23.

Jensen, Silicon-Based Microchemical Systems: Characteristics and Applications. *Mater. Res. Soc. Bull.* 2006, 31, 101-7.

Johnson et al., Numerical studies of steady flow dispersion at low Dean number in a gently curving tube. J Fluid Mechanics Digital Archive. 1986;172(-1):329-45.

Kablaoui et al., "Reductive Cyclization of Enones by a Titanium Catalyst," *J. Am. Chem. Soc.* 1995, 117, 6785-6786.

Kappe et al., Controlled Microwave Heating in Modern Organic Synthesis. *Angew. Chern. Int. Ed.* 2004, 43, 6250-84.

Kimura et al., "Novel and Highly Regio- and Stereoselective Nickel-Catalyzed Homoallylation of Benzaldehyde with 1,3-Dienes," *J. Am. Chem. Soc.* 1998, 120, 4033-4034.

Kravchenko et al., The effect of solvents on the rate of the aminolysis reactions of substituted α-oxides. Ukrainian Chemistry Journal. 1990;56(2):168-72.

Kumar et al., Phosphomolybdic acid-Al2O3: A mild, efficient, heterogeneous and reusable catalyst for regioselective opening of oxiranes with amines to β-amino alcohols. J. *Mol. Catal. A: Chern.* 2007, 266, 65.

Maheswara et al., Regioselective ring-opening of epoxides with amines using Zn(ClO4)2-Al2O3 as a heterogeneous and recyclable catalyst. *Tetrahedron Lett.* 2008, 49,1795.

Majewski et al., Stereoselective Synthesis of Protected Ketohexoses via Aldol Reaction of Chiral Dioxanone Enolate. Synlett. 1999;1999(9):1447-9.

Markert et al., Amine-catalyzed direct aldol addition. J Am Chem Soc. 2007;129:7258-9.

Marriner et al., "Metallo-Aldehyde Enolates via Enal Hydrogenation: Catalytic Cross Aldolization with Glyoxal Partners As Applied to the Synthesis of 3,5-Disubstituted Pyridazines," *J. Org. Chem.* 2003, 69, 1380-1382.

Maryanoff et al., Synthesis of phosphates and phosphate isosteres of furanose sugars as potential enzyme inhibitors. Tetrahedron. 1988;44:3093.

Mason et al., Greener Approaches to Organic Synthesis Using Microreactor Technology. Chem. Rev. 2007,107,2300-18.

Matsuda et al., Rhodium catalyzed direct coupling of αβ-unsaturated ketone, aldehyde, and trialkylsilane: An easy access to regio-defined aldol derivatives. *Tetrahedron Lett.* 1990, 31, 5331-5334.

McDonald., A new synthesis of d-psicose (d-ribo-hexulose). Carbohydro Res. 1967;5:106-8.

Miller et al., "Catalytic Asymmetric Reductive Coupling of Alkynes and Aldehydes: Enantioselective Synthesis of Allylic Alcohols α-Hydroxy Ketones," *J. Am. Chem. Soc.* 2003, 125, 3442-3443.

Mio et al., Synthetic studies on (+)-hydantocidin (3): a new synthetic method for construction of the spiro-hydantoin ring at the anomeric position of D-ribofuranose. Tetrahedron. 1991;47(12-13):2133-44.

Montgomery, J., Nickel-catalyzed reductive cyclizations and couplings. *Angew. Chem. Int. Ed.* 2004, 43, 3890-3908.

Morgenlie, Synthesis of Di-O-Isopropylidene derivates of L-fructose. Carbohydrate Res. 1982;107:137-41.

Moseley et al., Scaling-Out Pharmaceutical Reactions in an Automated Stop-Flow Microwave Reactor. *Org. Process Res. Dev.* 2008, 12,967-81.

(56) References Cited

OTHER PUBLICATIONS

Murphy et al., Accelerating Reactions with Microreactors at Elevated Temperatures and Pressures: Profiling Aminocarbonylation Reactions. *Angew. Chem. Int. Ed.* 2007,46, 1734-7.

Myint et al., Temperature-dependent diffusion coefficient of soluble substances during ethanol extraction of clove. J American Oil Chemists' Soc. 1996;73(5):603-10.

Ng et al., "Highly Enantioselective and Regioselective Nickel-Catalyzed Coupling of Allenes, Aldehydes, and Silanes," *J. Am. Chem. Soc.* 2005, 127, 7320-7321.

Ng et al., "Nickel-Catalyzed Coupling of Alkenes, Aldehydes, and Silyl Triflates," *J. Am. Chem. Soc.* 2006, 128, 11513-11528, as published online Aug. 10, 2006.

Ng et al.., "Simple Alkenes as Substitutes for Organometallic Reagents: Nickel-Catalyzed, Intermolecular Coupling of Aldehydes, Silyl Triflates, and Alpha Olefins," *J. Am. Chem. Soc.* 2005, 127(41), 14194-5.

Nieto et al., Practical synthesis of Shi's diester fructose derivative for catalytic asymmetric epoxidation of alkenes. J Org Chem. Nov. 25, 2005;70(24):10143-6.

Niu et al., Enantioselective Total Syntheses of [6R,7R] and [6S,7S] Tricyclic β-Lactams. J Org Chem. 1996;61(3):1014-22.

Oblinger et al., "A New Stereoselective Method for the Preparation of Allylic Alcohols," *J. Am. Chem. Soc.* 1997, 119, 9065-9066.

Oblinger, E. S., "Nickel-Catalyzed and Organozinc-Mediated Carbocyclizations and Three-Component Couplings," (Ph.D. Thesis, Wayne State University, 1997), 88 pages.

Ogoshi et al., "AlMe$_3$-Promoted Oxidative Cyclization of $h^2$-Alkene and $h^2$-Ketone on Nickel(0). Observation of Intermediate in Methyl Transfer Process," *J. Am. Chem. Soc.* 2005, 127(37), 12810-12811.

Ogoshi et al., "Direct Observation of Oxidative Cyclization of $h^2$-Alkene and $h^2$-Aldehyde on Ni(0) Center. Significant Alteration by Addition of Me$_3$-SiOTf," *J. Am. Chem. Soc.* 2004, 126(38), 11802-3.

Onaka et al., Zeolite-catalyzed ring-opening of epoxides with amines *Chem. Lett.* 1985;6:779-82.

Schmid et al., D-(R)-glyceraldehyde acetonide. Org Synth 1998;9:450.

Parker et al., Mechanisms of Epoxide Reactions. Chem. Rev. 1959;59(4):737-99.

Prashad et al., An Efficient and Economical Synthesis of 5,6-Diethyl-2,3-dihydro-1H-inden-2-amine Hydrochloride. J. *Org. Process Res. Dev.* 2006, 10,135-41.

Procopio et al., Highly efficient and versatile chemoselective addition of amines to epoxides in water catalyzed by erbium(III) triflate. *Tetrahedron Lett.* 2008,49,2289.

Ramasastry et al., Water-compatible organocatalysts for direct asymmetric syn-aldol reactions of dihydroxyacetone and aldehydes. Org Lett. Apr. 17, 2008;10(8):1621-4. Epub Mar 20, 2008.

Ramón et al., Asymmetric multicomponent reactions (AMCRs): the new frontier. *Angew. Chem. Int. Ed.* 2005, 44, 1602-1634.

Revis et al., Novel synthesis of β-siloxy esters by condensation of carbonyls and trimethylsilane with α,β-unsaturated esters catalyzed by RhC13. *Tetrahedron Lett.* 1987, 28, 4809-4812.

Roberge et al., Microreactor Technology and Continuous Processes in the Fine Chemical and Pharmaceutical Industry: Is the Revolution Underway? *Org. Process Res. Dev.* 2008, 12, 905-10.

Rogers et al., Comparative chemistry of the bay- and non-bay-region tetrahydro epoxides of phenanthrene. J. Am. Chem. Soc. 1979;101(16):4713-4719.

Sato et al., "Nickel-Catalyzed Intermolecular Coupling of 1,3-Dienes and Aldehydes via Transmetalation of Nickelacycles with Diisobutylaluminum Acetylacetonate," *J. Org. Chem.* 2002, 67, 656-662.

Shi et al., Synthesis of 1,2:4,5-di-o-isopropylidene-d-erythro-2,3-hexodiulo-2,6-pyranose. a highly enantioselective ketone catalyst for epoxidation Org Synth. 2003;80:1.

Shi et al., Practical synthesis of an 1-fructose-derived ketone catalyst for asymmetric epoxidation of olefins.J Org Chem. 2006;71:5377-9.

Shibuya et al., 2-Azaadamantane N-Oxyl (Azado) and 1-Me-Azado: Highly Efficient Organocatalysts for Oxidation of Alcohols. J Am Chem Soc. 2006;128(26):8412-3.

Sirovski et al., Large-scale fatty amine ethoxylation reactor: A dynamic model. Chemical Engineering Journal. 2006;117(3):197-203.

Sodeoka et al., New method for the stereocontrolled synthesis of silyl dienol ethers using (naphthalene)chromium tricarbonyl catalyzed isomerization. J Am Chem Soc. 1990;112(12): 4906-4911.

Sturton et al., Pharmacological Characterization of Indacaterol, a Novel Once Daily Inhaled β2 Adrenoceptor Agonist, on Small Airways in Human and Rat Precision-Cut Lung Slices. *J. Pharmacol. Exp. Ther.* 2008, 324, 270-5.

Sudarsan et al., Multivortex micromixing. PNAS. 2006;103(19):7228-33.

Sundaram et al., Kinetics of reactions of amines with alkene oxides. Bulletin of the Chemical Society of Japan. 1969;42(11):3141-7.

Takai et al., "Regioselective Reductive Coupling of Alkynes and Aldehydes Leading to Allylic Alcohols," *Org. Lett.* 2003, 5, 653-656.

Taylor et al., "Catalytic Diastereoselective Reductive Aldol Reaction: Optimization of Interdependent Reaction Variables by Arrayed Catalyst Evaluation," *J. Am. Chem. Soc.* 1999, 121, 12202-12203.

Tian et al., Electronic probing of ketone catalysts for asymmetric epoxidation. Search for more robust catalysts. Org Lett. Mar. 8, 2001;3(5):715-8.

Tipson et al., Cyclic acetals of ketoses : Part IV. Re-investigation of the oxidation of 1,2:4,5-DI-O-isopropylidene-β-D-fructopyranose with methyl sulfoxide—acetic anhydride. Carbohydro Res. Feb. 2, 1971;16(2):383-93.

Trejbal et al., Kinetics of ethylenediamine and piperazine ethoxylation. Reaction Kinetics and Catalysis Lett. 2004;82(2):339-46.

Trost et al., "Non-metathesis ruthenium-catalyzed C-C bond formation," *Chem. Rev.* 2001, 101, 2067-2096.

Tsujimoto, S., "Addition of aldehydes and their equivalents to electron-deficient alkenes using N-hydroxyphthalimide (NHPI) as a polarity-reversal catalyst," *Tet Lett.* 2003, 44, 5601-5604.

Tu et al., An Efficient Asymmetric Epoxidation Method for trans-Olefins Mediated by a Fructose-Derived Ketone. J Am Chem Soc. 1996;118:98067.

Utsumi et al., Mimicking aldolases through organocatalysis: syn-selective aldol reactions with protected dihydroxyacetone. Org Lett. 2007;9:3445-8.

Vijender et al., Amberlist-15 as heterogeneous reusable catalyst for regioselective ring opening of epoxides with amines under mild conditions. J. Mol. Catal. A: Chern. 2007, 266, 290.

Vinnik et al., Kinetic Method by Using Calorimetry to Mechanism of Epoxy-Amine Cure Reaction; Part II. On catalytic action of the amine excess. Journal of Thermal Analysis and Calorimetry. 2003;73:819-26.

Vinnik et al., Kinetic Method by Using Calorimetry to Mechanism of Epoxy-Amine Cure Reaction; Part V. Phenyl glycidyl ether—aniline. Journal of Thermal Analysis and Calorimetry. 2004;75:753-64.

Vinnik et al., Kinetic Method by Using Calorimetry to Mechanism of Epoxy-Amine Cure Reaction; Part I. Mangeldorf's Approach. Journal of Thermal Analysis and Calorimetry. 2003;73:807-17.

Voisin-Chiret et al., Synthesis of new L-ascorbic ferulic acid hybrids. Molecules. Nov. 17, 2007;12(11):2533-45.

Waagstein et al., Beneficial effects of metoprolol in idiopathic dilated cardiomyopathy. *Lancet* 1993;342(8885):1441-6.

Wang et al., An efficient catalytic asymmetric epoxidation method. J Am Chem Soc. 1997;119(46):11224-35.

Wender et al., "Bis(1.5-cyclooctadiene)nickel(0)," Encyclopedia of Reagents for Organic Synthesis, Article Online Posting Date: Sep. 15, 2006, 44 pages.

Wender et al., CAS: 149:30799, 2001.

Wiles et al., Continuous Flow Reactors, a Tool for the Modern Synthetic Chemist. *Eur. J. Org. Chern.* 2008, 1655-71.

(56) References Cited

OTHER PUBLICATIONS

Wiles et al., Improving chemical synthesis using flow reactors. *Expert Opin. Drug Discovery* 2007, 2, 1487-503.

Wong et al.,. Organocatalytic oxidation. Asymmetric epoxidation of olefins catalyzed by chiral ketones and iminium salts. Chem Rev. Sep. 2008;108(9):3958-87. Epub Jul. 1, 2008.

Yadav et al., An efficient protocol for regioselective ring opening of epoxides using samarium triflate: Synthesis of propranolol, atenolol and RO363. Mol. Catal. A: Chem. 2007,261,207.

Zaborenko et al., Synthesis and Kinetics of highly energetic intermediates by micromixers: direct multistep synthesis of sodium nitrotetrazolate. Industrial & Engineering Chem Res. 2010;49(9)9:4132-9.

Zaborenko et al., Kinetic and Scale-Up Investigations of Epoxide Aminolysis in Microreactors at High Temperatures and Pressures. Organic Process Research & Development. 2011;15:131-9.

Zhao et al., Practical synthesis of an L-fructose-derived ketone catalyst for asymmetric epoxidation of olefins. J Org Chem. Jul. 7, 2006;71(14):5377-9.

* cited by examiner

US 8,877,930 B2

CONTINUOUS FLOW SYNTHESIS OF AMINO ALCOHOLS USING MICROREACTORS

RELATED APPLICATIONS

This application claims priority under 35 U.S.C. §119(e) to co-pending U.S. Provisional Application Ser. No. 61/258,140, filed Nov. 4, 2009, entitled, "Continuous Flow Synthesis of Amino Alcohols Using Microreactors," the contents of which application are incorporated herein by reference in its entirety for all purposes.

FIELD OF THE INVENTION

The present invention relates to devices and methods involving the synthesis of amino alcohols.

BACKGROUND OF THE INVENTION

β-Amino alcohols are an important class of compounds to the synthetic and pharmaceutical communities. For example, Oxycontin®, Coreg®, and Toprol-XL® display this functional group pattern, and other pharmaceuticals like Zyvox® and Skelaxin® feature oxazolidones that can be formed through β-amino alcohol precursors. A variety of methods to construct β-amino alcohols have been studied, and one of the more frequently used approaches involves ring opening of epoxides with amine nucleophiles. Significant advances have been made in the promotion of epoxide aminolysis by addition of, for example, lanthanide triflates, Lewis acids, solid acid supports, or solvents such as water. However, while these methods are effective for relatively simple substrates, more complex cases, such as those commonly found in the pharmaceutical industry, are often incompatible with the reagents or conditions necessary for these transformations. Thus, alternative and more general methods of amino alcohol synthesis via epoxide-opening reactions is currently a significant need.

Microwave irradiation is often used to rapidly achieve high reaction temperatures and thus faster reaction rates. For example, studies have described microwave-assisted aminolysis of epoxides in an efficient and straightforward manner. Microwave irradiation may allow for improved reaction profiles, however, limitations in microwave penetration depth have hampered scale-up to the industrial realm and require the use of microwave generators.

SUMMARY OF THE INVENTION

The present invention provides various methods for synthesizing pharmaceutically active species, or intermediates thereof. In some embodiments, methods for synthesizing amino alcohols are provided. The method may comprise flowing a fluid sample comprising an epoxide species and an amine species into a microchannel; and reacting, in the microchannel, the epoxide species and the amine species to form an amino alcohol.

In some embodiments, the method may comprise reacting an epoxide species and an amine species for a reaction time of about 15 hours or less, to produce an amino alcohol in a yield of at least 50%.

In some embodiments, the method may comprise reacting an epoxide species and an amine species in the presence of water and at least one organic solvent to produce an amino alcohol in a yield of at least 50%.

The present invention also provides methods of synthesizing a pharmaceutically active species, or intermediate thereof, comprising flowing a fluid sample comprising a pharmaceutically active species precursor into a microchannel; and performing a chemical reaction, in the microchannel, to convert the pharmaceutically active species precursor to the pharmaceutically active species or intermediate thereof.

Figure 1:
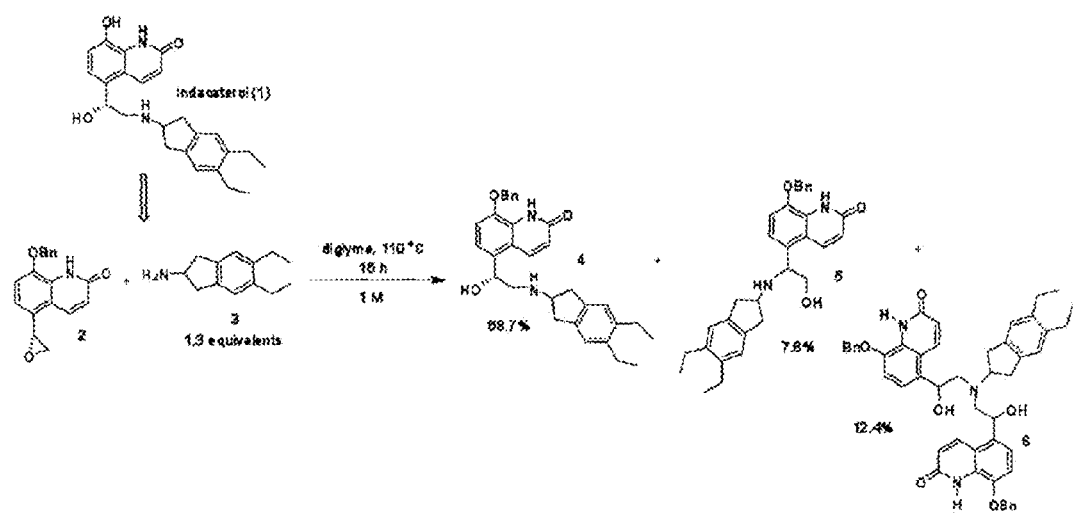
FIG. 1 illustrates an aminolysis reaction conducted in the synthesis of the chronic obstruction pulmonary disease (COPD) drug indacaterol 1.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention provides various methods for the synthesis of chemical species in a microreactor environment. In some cases, reaction products of the present invention may be valuable as intermediates and/or products in pharmaceutical and polymer research.

In some embodiments, methods described herein may provide the ability to perform chemical reactions with improved reaction profiles. For example, some embodiments may allow for the synthesis of a desired product using significantly reduced reaction times, relative to known methods, allowing for increased efficiency in the production of materials (e.g., pharmaceutically active materials). In some cases, continuous flow microreactors may be utilized to further reduce the time and cost required to synthesize such material. Some embodiments may also be capable of employing reaction conditions (e.g., high temperatures and pressures, volatile components) which may not be compatible with known processes (e.g., batch processes). Additionally, methods described herein have the further benefit of not requiring bulky, high power microwave generators.

In some embodiments, methods for synthesizing various species (e.g., pharmaceutically active species) in a microreactor are provided. For example, the method may involve flowing a fluid sample comprising one or more precursor species into a microchannel and performing a chemical reaction in the microchannel to convert the precursor species into a product. As used herein, the term "precursor" refers to a compound which may be converted to a final product (e.g., a β-amino alcohol) by one chemical reaction. The chemical reaction may be, for example, a substitution (e.g., $S_N1$, $S_N2$), elimination, coupling (e.g., metal-catalyzed coupling), oxidation, reduction, pericyclic (e.g., Diels-Alder, 1,2-dipolar cycloaddition), metathesis, isomerization, polymerization, protection, or deprotection reaction, or other types of intermolecular or intramolecular reactions known in the art. In some cases, the chemical reaction may involve a nucleophilic, ring-opening of an epoxide species (e.g., an aminolysis reaction). The product of the chemical reaction may be a pharmaceutically active species, such as a target drug, or may be an intermediate in the synthesis of a pharmaceutically active species.

The precursor species may be exposed to a set of conditions within the microchannel such that a chemical reaction or other transformation takes place. For example, a precursor species may be reacted at high temperature and pressure to produce a desired product (e.g., a β-amino alcohol). As used herein, the term "reacting" refers to the forming of one or more bonds between two or more components to produce a stable, isolable compound (intermolecular reaction) or the forming of one or more bonds between two or more parts of the same molecule to form a stable, isolable compound (intramolecular reaction). For example, a first precursor species and a second precursor species may react to form one reaction product comprising the first precursor species and the second precursor species joined by a covalent bond. That is, the term "reacting" does not refer to the interaction of solvents, catalysts, bases, ligands, or other materials which may serve to promote the occurrence of the reaction with the component(s). A "stable, isolable compound" refers to isolated reaction products and does not refer to unstable intermediates or transition states.

The fluid sample may be introduced into a reaction region of a microreactor and may be exposed to a set of conditions, including temperature, pressure, and the like, in order to facilitate the occurrence of a chemical reaction within the microchannel. In some cases, the fluid sample may be flowed into a region of the microreactor (e.g., a mixing region) where the various components are mixed together to produce a homogeneous or heterogeneous fluid sample, prior to introduction into the reaction region. For example, a first precursor species and a second precursor species may be separately introduced into the microreactor, via two different inlets, and may be combined in a mixing region of the microreactor. The combined fluid sample may then be flowed into a reaction region in order to perform the chemical reaction.

Figure 3:
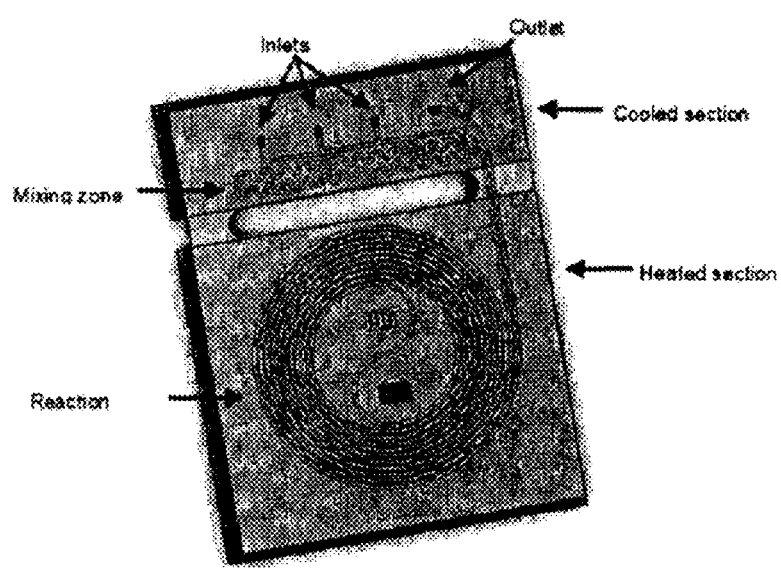
FIG. 3 shows a diagram of a microreactor for epoxide aminolysis, according to one embodiment.

FIG. 3 shows an illustrative embodiment of a microreactor, comprising at least one inlet in fluid communication with a reaction region, in which reaction of chemical species may be performed. The microreactor also includes an outlet in fluid communication with the reaction region, through which the product of the reaction may be transferred. In operation, a fluid sample comprising chemical species may be introduced into the reaction region via the inlet(s), and, upon reaction, the fluid sample may be removed from the microreactor via the outlet. The microreactor may also comprise a mixing zone, in fluid communication with the inlet and the reaction region, for pre-mixing of the fluid sample prior to introduction into the reaction region.

In some cases, the method may comprise synthesis of a pharmaceutically active species or intermediate thereof. As used herein, the term "intermediate" refers to a compound which may be converted to a final product by one or more chemical reactions. Typically, the intermediate compound comprises a substantial portion of the desired, reaction product. The method may involve flowing a fluid sample that includes a pharmaceutically active species precursor, one or more fluid carriers (e.g., solvents), and additional components (e.g., catalysts, acids, bases, ligands, etc.), into a microchannel. A chemical reaction to convert the pharmaceutically active species precursor to the pharmaceutically active species, or intermediate thereof, may then be performed in the microchannel. In some embodiments, the method further comprises reacting an intermediate of the pharmaceutically active species to produce the pharmaceutically active species. For example, a pharmaceutically active species precursor may be reacted to produce a pharmaceutically active intermediate species, such as a β-amino alcohol comprising a protecting group, which may then be further reacted, for example, via a deprotection step, to produce the final pharmaceutically active species. As used herein, a "pharmaceutically active species" refers to any species capable of interacting with (e.g., having activity for) a chemical or biological target to produce a desired therapeutic effect in a subject. In some cases, the pharmaceutically active species may aid in the prevention, minimization, or reversal of disease progression, i.e., as monitored by clinical observations, and/or laboratory and imaging investigations apparent to one of ordinary skill in the art. In some embodiments, the pharmaceutically active species may be a small molecule, such as indacaterol or metoprolol.

In one set of embodiments, amino alcohols (e.g., β-amino alcohols) may be synthesized in a microreactor. For example, the synthesis may involve an aminolysis reaction between an epoxide species and an amine species, i.e., an epoxide species may undergo a ring-opening reaction in the presence of an amine species to produce a β-amino alcohol, as shown in Scheme 1. The method may involve flowing a fluid sample comprising an epoxide species and an amine species into a microchannel and reacting, in the microchannel, the epoxide species and the amine species to form an amino alcohol. In one embodiment, the reaction may be intermolecular. That is, prior to the reaction the epoxide species and the amine species are not contained within the same molecule, i.e., the amine and the epoxide species are not joined to one another, i.e., neither directly (by one or more bonds), nor by a series bonds consisting of one or more atoms or functional groups. In another embodiment, the reaction may be intramolecular.

Scheme 1

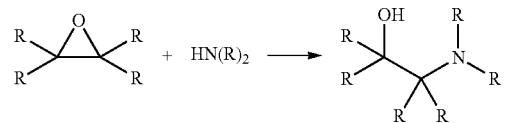

In some cases, the method involves reacting an epoxide species and an amine species for a reaction time of about 15 hours or less, to produce an amino alcohol in a yield of at least 50%. In some cases, the epoxide species and an amine species are reacted for a reaction time of about 10 hours or less, about 5 hours or less, about 3 hours or less, or, in some cases, about 1 hour or less, to produce an amino alcohol in a yield of at least 50%. In one set of embodiments, the epoxide species and an amine species are reacted for about 30 minutes to about 1 hour, to produce an amino alcohol in a yield of at least 50%. It should be understood that reaction times of less than 30 minutes (e.g., 5 minutes, 10 minutes, 15 minutes, etc.) may also be utilized, and those of skill in the art would be able to select appropriate reaction conditions suitable for use in a particular application. In some cases, the amino alcohol is produced in a yield of at least 50%, at least 60%, at least 70%, at least 80%, at least 90%, at least 95%, at least 97%, or, in some cases, at least 99%. In some embodiments, the amino alcohol is produced in quantitative yield (e.g., 100%).

In some embodiments, the aminolysis reaction between the epoxide species and the amine species may be performed without need for additives or promoters, such as Lewis acids or strong bases, in order to produce the amino alcohol product. As described more fully below, the fluid sample may be exposed to a set of conditions within the microchannel sufficient to convert the epoxide species and the amine species into the desired amino alcohol, in the absence of a Lewis acid or strong base.

In some cases, nucleophilic attack of the epoxide species may occur at one or more sites on the epoxide species. Some embodiments may involve nucleophilic attack at a less sterically hindered site of the epoxide species, i.e., at a site comprising fewer substituents and/or substituents which are relatively smaller in size. In some cases, the reaction product obtained may be from the nucleophilic attack at the α-terminal end of the epoxide. Additives that may promote regioselective attack at a particular site of the epoxide species may be included in the reaction mixture, such as a polar protic solvent (e.g., ethanol, water, NMP, acetonitrile, etc.).

In an illustrative embodiment, epoxide aminolysis may be utilized in a continuous flow microreactor to produce an intermediate of the drug indacaterol. Indacaterol has been used in the treatment of chronic obstructive pulmonary disease (COPD) and has shown promise as a one-dose daily bronchodilator. For example, the method may comprise the reaction represented by Scheme 2.

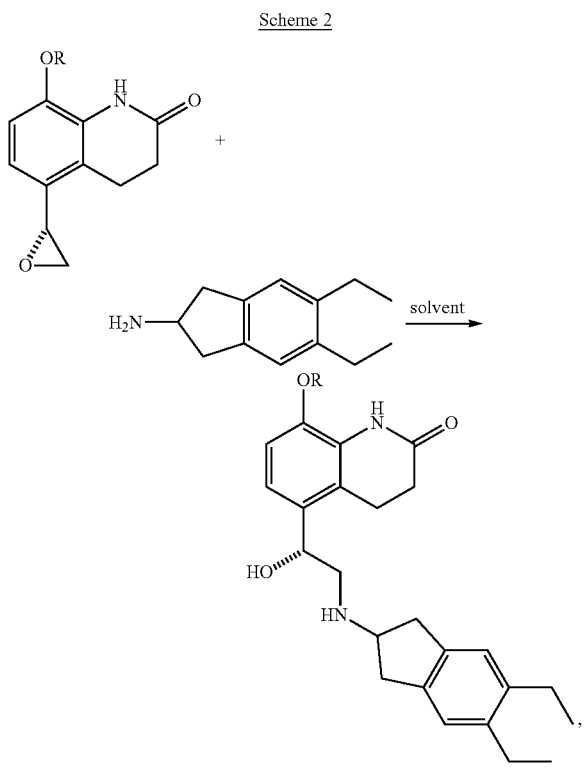

wherein R is a protecting group. In some cases, R is benzyl. The final indacaterol product may be obtained by a deprotection step to cleave the protecting group.

In another embodiment, epoxide aminolysis may be carried out in a microreactor to produce the drug metoprolol, a β-amino alcohol and a selective $β_1$-ladrenoreceptor blocking agent used in the treatment of hypertension. The method may comprise the reaction represented by Scheme 3.

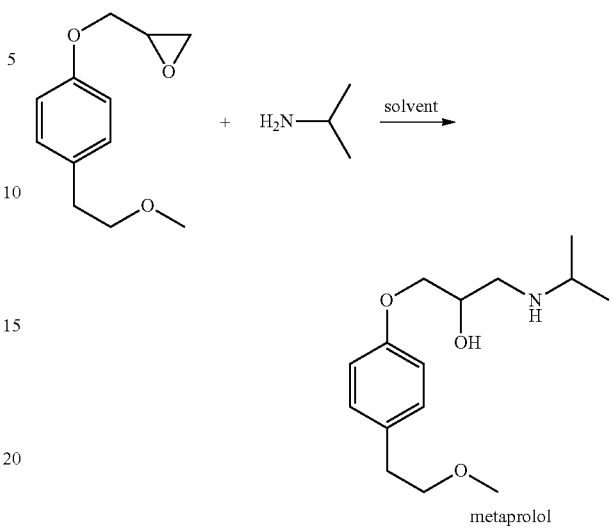

An advantageous feature of some embodiments is the ability to perform chemical reactions in a continuous flow process. That is, the method may involve use of a microreactor system comprising a series of regions fluidly connected to one another and arranged in tandem within a continuous channel. In some embodiments, each region of the microreactor system may capable of subjecting the fluid sample to the same set of reaction conditions such that numerous reaction regions may be operated in parallel. In some embodiments, at least two of the regions in the microchannel may be capable of exposing the fluid sample to different sets of reaction conditions. For example, a fluid sample may be introduced to a first region of the microchannel, in which a first chemical reaction or chemical process (e.g., separation, purification, etc.) is performed. The fluid sample may then be flowed into a second region of the microchannel, in which a second chemical reaction or chemical process may be performed. Use of such configurations may be advantageous in that a precursor species may be reacted, separated, and/or purified at multiple locations within the microreactor system, allowing for execution of a multi-step synthesis in a single, continuous process. In some cases, the reaction profile (e.g., reaction time, overall yield, distribution of reaction products, etc.) may be substantially independent of fluid sample volume, such that the chemical reaction may be performed at larger scales without substantial change in reaction profile.

In some embodiments, the use of a microreactor (e.g., a continuous flow microreactor) may allow for a highly efficient synthetic process. For example, a desired product may be synthesized using relatively shorter reaction times, relative to known methods. In some embodiments, the method may involve reacting a precursor species for a reaction time of about 15 hours or less, to produce a desired reaction product in a yield of at least 50%. In some embodiments, the reaction time may be about 10 hours or less, about 5 hours or less, about 3 hours or less, or, in some cases, about 1 hour or less (e.g., 30-60 minutes). Without wishing to be bound by theory, such reaction times may be attributed to increases in the rate of a chemical reaction within a microreactor, relative to other processes (e.g., batch processes), due to rapid mass and heat transfer, high temperatures, and high pressures attainable within a microreactor, as described more fully below.

The use of microreactors may provide additional advantages in that certain reaction conditions, precursor species, and/or combinations thereof, may be used that may have otherwise been unsuccessful in batch processes. For example, various solvents and solvent combinations may be employed in methods described herein. In some cases, volatile solvents, which may hinder chemical reactions in batch processes, may be utilized without a substantial decrease in reaction efficiency. Typically, systems for batch processes include a significant amount of headspace directly above the surface of the reaction mixture, which may allow volatile components in the mixture to vaporize, altering the composition of the reaction mixture/reaction products and affecting the efficiency of the reaction. Additionally, in batch processes, the relative boiling point of the reaction mixture components must be compatible with one another, which can often limit the range of solvents and material that can be utilized. Using a microreactor, the available headspace is substantially decreased or eliminated, allowing for the use of more volatile solvents or other components without loss in reaction rate/efficiency.

For example, the solvent(s) may comprise organic solvents, aqueous solvents, and mixtures thereof. In some embodiments, polar aprotic solvents may be included in the fluid sample in order to enhance selectivity in chemical reactions (e.g., aminolysis reactions). In some cases, mixtures polar aprotic and polar protic solvents can be employed to accelerate a chemical reaction in a microreactor, without concern for the volatility or relative boiling points of the solvent components. This can allow for a wide range of solvent combinations capable of substantially dissolving numerous precursor species and reaction products, including those which may be substantially incompatible with (e.g., insoluble in) solvents having low volatility. For example, numerous pharmaceutically active species may be substantially soluble in aqueous solutions, or solutions comprising an aqueous component. In some cases, the solvent may comprise at least organic solvent and at least one aqueous solvent. In one set of embodiments, the chemical reaction is performed in the presence N-methyl pyrrolidone and water.

Other components of the fluid sample may also comprise volatile species due to the elimination of headspace within the microreactor. For example, one or more precursor species may comprise a relatively low boiling point. In reactions involving an amine species, the method may advantageously comprise the use of volatile amines without substantially affecting the rate of the reaction or the product distribution of the reaction.

In some embodiments, the use of a continuous flow microreactor provides the ability to maintain temperatures and pressures that are not readily attainable in batch processes. In some cases, the chemical reaction is performed at a temperature of at least 75° C., at least 100° C., at least 125° C., at least 150° C., at least 175° C., at least 200° C., at least 225° C., at least 250° C., at least 275° C., at least 300° C., or, in some cases, greater. In some cases, the chemical reaction is performed at a pressure of at least 100 psi, at least 125 psi, at least 150 psi, at least 175 psi, at least 200 psi, at least 225 psi, at least 250 psi, at least 275 psi, at least 300 psi, at least 400 psi, at least 500 psi, or, in some cases, greater. The use of elevated temperatures and pressures may facilitate conversion of the precursor species into a reaction product, without need for additives or promoter species.

In one set of embodiments, the method involves reacting an epoxide species and an amine species at a temperature of at least 75° C. and at a pressure of at least 100 psi.

The methods may comprise additional steps, including sterilization of the pharmaceutically active species, for example, by filtration or by incorporating sterilizing agents in the form of sterile solid compositions that can be dissolved in sterile water, or some other sterile injectable medium immediately before use. In some embodiments, the pharmaceutically active species may be mixed under sterile conditions with a pharmaceutically-acceptable carrier, or with any preservatives, buffers, propellants, isotonic aqueous or nonaqueous solutions, dispersions, suspensions or emulsions, or sterile powders.

In some cases, the method may also comprise determination of the activity of the pharmaceutically active species. For example, the pharmaceutically active species may be evaluated for its activity against a particular chemical or biological target using various assays (e.g., in vitro assays, in vivo assays) known in the art.

As used herein, the terms "microreactor" and "microfluidic device" are given their ordinary meaning in the art and refer to devices having components, such as conduits, channels, reservoirs, enclosures, and the like, which have maximum cross-sectional dimensions less than 2 mm, and in some cases, less than 1 mm In one set of embodiments, components of embodiments of the invention are microfluidic or have a largest cross sectional dimension of no more than 2 mm or 1 mm Of course, larger channels, tubes, chambers, reservoirs, etc. can be used to store fluids in bulk and to deliver fluids to components of the invention. In one set of embodiments, the maximum cross-sectional dimension of the components of embodiments of the invention are less than 500 microns, less than 200 microns, less than 100 microns, less than 50 microns, or less than 25 microns. In some cases the dimensions of the component may be chosen such that fluid is able to freely flow through the article or substrate. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As used herein, the term "microchannel" refers to a region in a microreactor through which a fluid sample may be flowed. The microchannel may have any dimension suited for a particular application. In some cases, the microchannel may have a cross sectional dimension of 0.01 mm, 0.05 mm, 0.1 mm, 0.5 mm, 1.0 mm, 3.0 mm, 5.0 mm, 10 mm, 50 mm, 100 mm, or greater. In some embodiments, the channel cross section may be 1.0 mm or 3.0 mm Cross section, in this context, is measured perpendicular to the central axis of a channel. In some cases, the channel is sized such that all cross sections at one or more locations in the channel (i.e., all dimensions perpendicular to the central axis) have dimensions as noted above. In some cases, the device may have at least one cross-sectional dimension less than 10 mm, less than 5.0 mm, less than 3.0 mm, less than 1.0 mm, or less than 0.5 mm The length of the channel, or the length of an individual region in a tandem device, may be, for example, 5.0 mm, 10 mm, 20 mm, 30mm, 50 mm, 100 mm, or greater.

Devices described herein can be fabricated of a polymer, for example an elastomeric material such as poly(dimethylsiloxane) (PDMS) using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the network, a flat substrate, for example, a glass slide, silicon wafer, or polystyrene surface may be placed against the PDMS surface and may be held in place by van der Waals forces, or may be fixed to the PDMS using an adhesive. To allow for the introduction and receiving of fluids to and from the network, holes (e.g., 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue. Examples of methods of manufacturing devices such as these are provided in U.S. Pat. No. 6,645,432 and K. F. Jensen, "Silicon based microchemical systems—Characteristics and applications," *Materials Research Society Bulletin* 31, 101-107 (2006), both of which are incorporated by reference in their entirety for all purposes.

The microreactor system may be designed and fabricated to be capable of withstanding a wide range of solvents and chemical conditions, including high temperature, high pressure, exposure to various solvents and reagents, and the like. In some cases, a silicon microreactor system may be used. The microreactor may include channels coated with, for example, silicon nitride to provide chemical resistance, enabling the reactor to withstand slightly basic conditions at high temperatures.

The devices and methods as described herein may further comprise other components, such as various sensors, controllers, optical fibers, membranes, conduits, enclosures, valves, and the like, as required for a particular application. Such components may be fabricated using methods known in the art, such as micromachining, etching, lithography, and the like.

The term "epoxide species" refers to any compound comprising an epoxide group, i.e., a three-membered ring comprising two carbon atoms and one oxygen atom. The epoxide species may be selected to be capable of undergoing a ring-opening reaction, i.e., via interaction with a nucleophile such as an amine species. In some embodiments, the epoxide species may be monosubstituted, disubstituted, or, in some cases, trisubstituted. In some embodiments, the epoxide species has the formula,

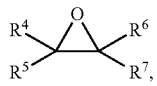

wherein $R^4$, $R^5$, $R^6$, and $R^7$ can the same or different and are hydrogen, alkyl, heteroalkyl, aryl, heteroaryl, a carbonyl group, any of which may be substituted; or, any of $R^4$, $R^5$, $R^6$, and $R^7$ may be joined to form a ring, optionally substituted. In some embodiments $R^4$, $R^5$, and $R^6$ are each hydrogen.

The amine species may be selected to exhibit sufficient nucleophilicity in the presence of, for example, an epoxide species. In some embodiments, the amine may be a monosubstituted, disubstituted, or, in some cases, trisubstituted species. In some embodiments, the amine species has the formula, $NR^1R^2R^3$, wherein $R^1$, $R^2$, and $R^3$ can the same or different and are hydrogen, alkyl, heteroalkyl, aryl, heteroaryl, a carbonyl group, any of which may be substituted; or, any of $R^1$, $R^2$, and $R^3$ may be joined to form a ring, optionally substituted. In some cases, the amine species has the formula, $NH_2R^3$.

Certain screening tests may be employed to determine which epoxides and amines may be preferred for use in methods described herein. For example, in some embodiments, amine species which are substituted with at least one hydrogen may be utilized. As methods of the invention can easily be carried out and require relatively short reaction times, a wide ranges of epoxides and amines may be tested simply by subjecting them to reaction methods described herein. For example, reaction conditions may be readily screened by altering temperature, pressure, and flow rate of the fluid sample(s).

As noted herein, the method may be performed in the presence of one or more fluid carriers. In some cases, the method involves use of at least one organic solvent. Examples of some organic solvents include benzene, naphthalene, p-cresol, toluene, xylene, diethyl ether, glycol monomethyl or dimethyl ether, petroleum ether, hexane, cyclohexane, methylene chloride, chloroform, carbon tetrachloride, alcohol (e.g., methanol, ethanol, etc.), dioxane, tetrahydrofuran (THF), dimethyl sulfoxide, dimethylformamide, N-methyl pyrrolidone (NMP), hexamethyl-phosphoric triamide, ethyl acetate, pyridine, triethylamine, picoline, mixtures thereof, or the like. In some embodiments, the organic solvent is an alcohol, naphthalene, or N-methyl pyrrolidone. In some embodiments, the organic solvent is N-methyl pyrrolidone. The fluid carrier may also comprise an aqueous solvent such as water. In some embodiments, the fluid carrier is a mixture of N-methyl pyrrolidone and water.

The products which may be produced by methods described herein may undergo further reaction(s) to afford desired products or derivatives thereof. Such permissible derivatization reactions can be carried out in accordance with conventional procedures known in the art. For example, potential derivatization reactions include a deprotection step to cleave a protecting group from the final product. The phrase "protecting group" is given its ordinary meaning in the art and refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, a "fluid" may refer to essentially any fluent material in a liquid, gas, and/or supercritical state. In some cases, the fluid comprises at least one component able to undergo a chemical or biological process (e.g., chemical reaction, separation, etc.). The fluid sample and microchannel may be selected in combination with each other to carry out a particular chemical or biological process. For example, the fluid may comprise components able to be separated from one another upon contact with a particular surface in a separation device. In one set of embodiments, the interacting fluid may comprise a chemical compound or other chemical substrate able to react with a catalyst or other species contained within a reactor device, or other reagent introduced into the reactor device for the purpose of reacting with the chemical compound or chemical substrate.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized
in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, heteroalkyl, aryl, or heteroaryl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R') (R")(R''') wherein R', R", and R''' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES AND EMBODIMENTS

The following examples focus on adapting pharmaceutically prevalent batch reactions, such as β-amino alcohol formation through epoxide aminolysis, to a continuous flow microreactor process.

In summary, the aminolysis of epoxides using a continuous flow microreactor proved to be a highly efficient process. Excellent yields and conversions with simple terminal epoxides can be obtained at residence times under 5 min in ethanol under high temperature and pressure. The aminolysis of more sterically hindered epoxides also proved successful. The continuous flow microreactor is capable of reaching temperatures that are not attainable in microwave batch processes, and due to the elimination of headspace, volatile amines can be used in the reaction without affecting overall product distributions. The use of a small amount of a polar protic solvent to accelerate the aminolysis reaction can also be applied without concern for the volatility of the solvent components. Application of epoxide aminolysis in a continuous flow microreactor towards the production of metoprolol led to product outputs of 7.0 g/h (approximately 60 kg/year). In another example, the penultimate version of indacaterol was also produced by this method at a residence time that was 1/60$^{th}$ of that reported in the literature, yet with similar yield.

Example 1

Figure 4:
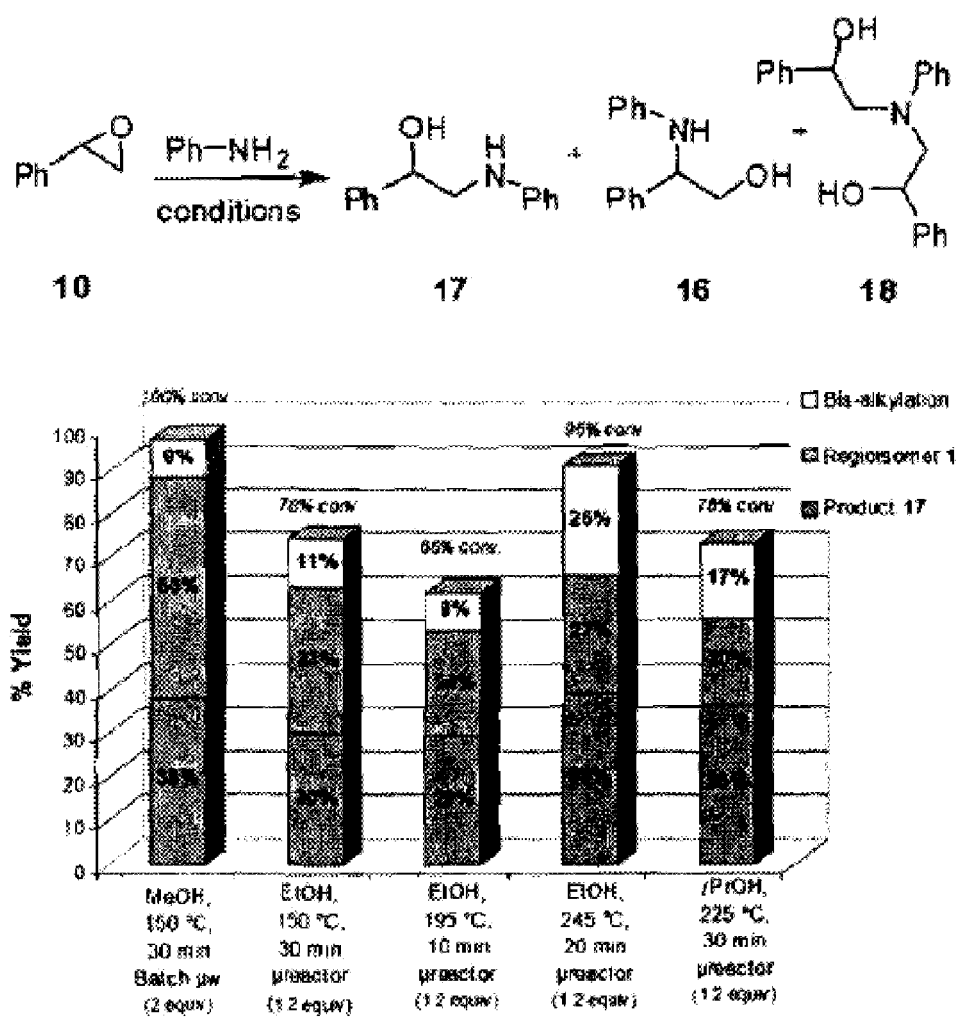
FIG. 4 shows a graph comparing the ratio of regioselective products formed in the aminolysis of styrene oxide with aniline, using different reaction conditions.

The following example describes the fabrication of a microfluidic system used in the synthesis of β-amino alcohols. A silicon microreactor system was used, providing a chemically and physically robust environment capable of rapid thermal equilibration. (FIGS. 3-4) The silicon channels were coated with silicon nitride to provide chemical resistance, enabling the reactor to withstand slightly basic conditions at high temperatures. Combined with Kalrez (a fluoroelastomer) o-rings, the reactor system is capable of withstanding a wide range of solvents and chemical conditions. The elasticity of the O-rings and rigidity of silicon easily allowed for pressurization up to 500 psi.

Interfacial forces are often dominant at the microfluidic scale. Combined with the smoothness of the channel walls, these forces can result in the experimental observation of solvent superheating to temperatures above boiling. Using the Antoine equation, the boiling points for ethanol and acetonitrile were calculated at 250 psi to be at 174° C. and 208° C., respectively, and at 500 psi, 206° C. and 259° C., respectively. However, within the microreactor, pure ethanol was not observed to boil at 250 psi until 217° C. was attained, with freshly incoming material ceasing to boil (flash) when the reactor was cooled to 206° C. At 500 psi, ethanol did not boil until 250° C., with flashing ceasing when cooled to 246° C. A similar effect was observed with acetonitrile, which, at 250 psi, only boiled at 246° C., ceasing at 239° C. At 500 psi, boiling was not achieved even when heated to 300° C. Thus, the dominance of interfacial forces over gravity and inertial ones on the microscale further can extend the range of operating temperatures beyond even those afforded by the pressurization.

The high thermal conductivity of silicon can greatly aid in spreading heat and can significantly reduce the occurrence of hot spots. The use of aluminum for the heating chuck and of graphite as the liner between the chuck and the reactor further helped distribute the heat while providing high heat transfer. Additionally, the spiral channel layout helped to reduce the effect of any inhomogeneity in temperature on the reaction. The etched-out area of the reactor established thermal separation between the inlet/outlet area (including the mixing zone) and the reaction area of the reactor. This allowed the area in contact with polymer o-rings and fittings to remain at near room temperature when the compression chuck was water-cooled, while the reaction zone was at temperatures of up to 300° C. In addition to enabling simple fluidic packaging, the small volumes within the microreactor allowed the reaction mixture to be rapidly brought to room temperature upon leaving the reaction zone, providing highly efficient quenching and accurate residence time evaluation.

Example 2

The following example describes the general aminolysis of epoxides using a microreactor. In order to test the limitations and effectiveness of microreactors in the aminolysis of epoxides, a variety of substrates were investigated. Of particular interest was the direct comparison of results obtained under standard batch microwave protocols and those obtained using the microreactor under similar conditions. An additional factor considered was that the microreactor setup is capable of operating at higher temperatures than those ultimately obtained in the microwave due to higher pressure tolerances. Ethanol was chosen as the initial solvent due to its good solvating properties, high dielectric constant, and low toxicity. The results of these reactions are summarized in Table 1.

TABLE 1

General aminolysis reactions performed in a continuous-flow microreactor.

| Expoxide | Amine | Entry | Conditions (psi) | Amine Equiv | Temp (° C.) | Flow rate (μL/min) | Time | Product (α-Opened) (%) | Isomer (β-Opened) (%) | Bis-alkyl (%) | conv. (%) |
|---|---|---|---|---|---|---|---|---|---|---|---|
| 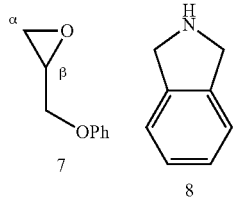 7 | 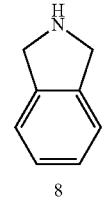 8 | 1 | Batch μ$_W$ | 1.2 | 150 | — | 30 min | 72 | — | 26 | >99 |
| | | 2 | μ$_{reactor}$ (250) | 1.2 | 150 | 4 | 30 min | 73 | — | 26 | >99 |
| | | 3 | μ$_{reactor}$ (250) | 1.2 | 195 | 60 | 2 min | 72 | — | 24 | 98 |
| | | 4 | μ$_{reactor}$ (250) | 1.2 | 195 | 120 | 1 min | 71 | — | 21 | 93 |
| 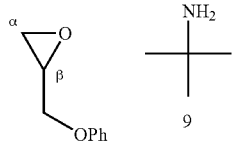 7 | 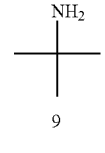 9 | 5 | Batch μ$_W$ | 1.2 | 150 | — | 30 min | 75 | — | 24 | >99 |
| | | 6 | Batch μ$_W$ | 1.2 | 150 | — | 30 min | 82 | — | 17 | >99 |
| | | 7 | μ$_{reactor}$ (250) | 1.2 | 150 | 4 | 30 min | 82 | — | 16 | >99 |
| | | 8 | μ$_{reactor}$ (250) | 1.2 | 195 | 40 | 3 min | 82 | — | 13 | 98 |
| | | 9 | μ$_{reactor}$ (250) | 2.0 | 195 | 120 | 1 min | 84 | — | 6 | 92 |

TABLE 1-continued

General aminolysis reactions performed in a continuous-flow microreactor.

| Expoxide | Amine | Entry | Conditions (psi) | Amine Equiv | Temp (° C.) | Flow rate (μL/min) | Time | Product (α-Opened) (%) | Isomer (β-Opened) (%) | Bis-alkyl (%) | conv. (%) |
|---|---|---|---|---|---|---|---|---|---|---|---|
| 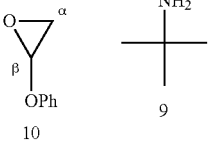 10 |  9 | 10 | Batch μ$_W$ | 1.2 | 150 | — | 30 min | 57 | 7 | 21 | 90 |
|  |  | 11 | Batch μ$_W$ | 1.2 | 150 | — | 30 min | 62 | 10 | 19 | 97 |
|  |  | 12 | μ$_{reactor}$(250) | 1.2 | 150 | 4 | 30 min | 62 | 7 | 16 | 94 |
|  |  | 13 | μ$_{reactor}$(250) | 1.2 | 195 | 24 | 5 min | 60 | 8 | 14 | 91 |
|  |  | 14 | μ$_{reactor}$(250) | 2.0 | 195 | 24 | 5 min | 66 | 9 | 8 | 91 |
| 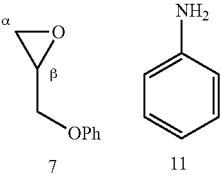 7 |  11 | 15 | Batch μ$_W$ | 1.2 | 150 | — | 30 min | 72 | — | 25 | >99 |
|  |  | 16 | μ$_{reactor}$(250) | 1.2 | 195 | 24 | 5 min | 63 | — | 18 | 82 |
|  |  | 17 | μ$_{reactor}$(250) | 2.0 | 195 | 24 | 5 min | 81 | — | 13 | 95 |
| 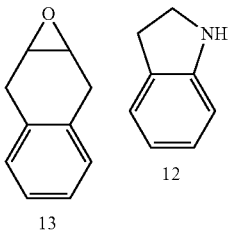 13 |  12 | 18 | Batch μ$_W$ | 1.2 | 150 | — | 30 min | 54 | — | — | 58 |
|  |  | 19 | μ$_{reactor}$(250) | 1.2 | 150 | 4 | 30 min | 39 | — | — | 40 |
|  |  | 20 | μ$_{reactor}$(250) | 1.2 | 195 | 4 | 30 min | 66 | — | — | 72 |
|  |  | 21 | μ$_{reactor}$(500) | 1.2 | 245 | 4 | 30 min | 71 | — | — | 93 |
| 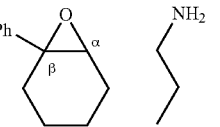 15 |  14 | 22 | Batch μ$_W$ | 5.0 | 150 | — | 30 min | 19 | 3 | — | 22 |
|  |  | 23 | μ$_{reactor}$(250) | 5.0 | 150 | 4 | 30 min | 15 | 2 | — | 17 |
|  |  | 24 | μ$_{reactor}$(500) | 5.0 | 240 | 4 | 30 min | 68 | 6 | — | 78 |

The ring opening of phenyl glycidyl ether 7 with 2-aminoindan 8 was first investigated. Under microwave irradiation in a sealed vial, complete conversion was obtained in 30 min at 150° C. (Table 1, Entry 1). The pressures attained in a 5 mL vial with 1 mL of solution ranged anywhere from 100 to 130 psi during the course of the reaction. The major product obtained resulted from nucleophilic attack at the alpha-terminal end of the epoxide ($S_N2$), and only minor isolated amounts (~1-2%, not quantified by HPLC analysis) of the regioisomer were observed. Formation of the bisalkylated product, derived from the subsequent reaction of the product with an additional equivalent of the epoxide, was also prevalent in this example and overall mass balances were excellent. In the microreactor system, the two reaction components were dissolved separately in ethanol (2 M solution of phenyl glycidyl ether, 2.4 M solution of 2-aminoindan) and introduced into the reactor via separate syringes at identical volumetric flow rates. Using a 250 psi backpressure regulator and a flow rate of 4 μL/min (30 min residence time) at 150° C., complete conversion was obtained in the microreactor and product distributions mirrored those of the microwave experiment (Table 1, Entry 2). With an epoxide concentration of 1 M and 250 psi of backpressure, ethanol was easily superheated to 195° C. without boiling being observed in the microreactor. Near complete conversion was realized at this temperature in 2 min, while good conversion (93%) was also observed at residence times of 1 min, corresponding to a flow rate of 120 μL/min (Table 1, Entries 2 and 3).

The role of volatile amines in epoxide aminolysis was investigated to study the benefits of microreactors over typical batch conditions. tert-Butylamine 9 was utilized for this study due to its relatively low boiling point (46° C.) and because it enabled the examination of a relatively hindered substrate. Opening of phenyl glycidyl ether at the terminal position of the epoxide was complete after microwave irradiation for 30 min However, the product distributions were found to be dictated by the reaction volumes (Table 1, Entries 5 and 6). Significant increases in the amount of bis-alkylation by product were observed when 1 mL of solution was heated in a 5 mL sealed vial, whereas 2 mL of the reaction mixture gave improved results. Without wishing to be bound by theory, this variance may be attributed to the reduction in available headspace and concomitant decrease in the amount of amine in the vapor phase. Since the amine is more volatile than the solvent, its vaporization decreases its concentration in solution, reducing the reaction efficiency. In contrast, the absence of headspace in the continuous-flow microreactor led to consistent product distributions, independent of reaction volumes (Table 1, Entry 7). When this volatile amine was used, reaction temperatures could also be maintained at 195° C. to afford almost complete conversion with residence times of 3 min (Table 1, Entries 8 and 9). Product distribution as a function of vial headspace was also observed in the opening of styrene oxide 10 with tert-butylamine (Table 1, Entries 10-12). When the amine reagent feed was increased to 4.0 M (2 equiv), reaction temperatures could be maintained at 195° C. without boiling in the microreactor and, as expected, a reduction in the amount of bis-alkylation was observed (Table 1, Entry 14). In addition, the proportion of regioisomer obtained by nucleophilic attack at the p-benzylic position ($S_N2$) of styrene oxide remained relatively constant throughout the trials and was not noticeably affected by increasing temperature.

Opening phenyl glycidyl ether with a less nucleophilic amine such as aniline 11 again resulted in the major product arising from attack at the terminal position along with some bis-alkylation by-product. High conversions could still obtained with 1.2 equiv of amine at the highest attainable temperatures in the microreactor with a residence time of 5 min (Table 1, Entry 16). Increasing the concentration of the amine resulted in higher overall conversions and improved yields for the mono-alkylated product (Table 1, Entry 17).

Internal and trisubstituted epoxides were also examined under microreactor conditions. Using the hindered secondary amine, indoline 12, and 1,4-dihydronaphthalene oxide 13, aminolysis was conducted both in the microwave and microreactor at 150° C. (Table 1, Entries 18 and 19). Moderate substrate conversion was obtained in each case. Without wishing to be bound by theory, the higher conversions observed in the microwave process compared to the microreactor can be attributed to two factors. First, the overall concentration in a microwave vial can be somewhat higher due to the headspace available to volatilize the solvent. Second, microwave reaction times can be slightly extended due to periods of warming and cooling during the pre-and post-reaction phases. Since microreactors take advantage of large surface-to-volume ratios, high reaction temperatures can be achieved rapidly and passage through the "cooling zone" allows for a similar prompt lowering of the overall temperature after the reaction. Increasing the temperature to 195° C. led to higher conversions after 30 min in this example (Table 1, Entry 20). Replacement of the 250 psi backpressure regulator in the initial microreactor setup with a 500 psi regulator allowed for superheating of ethanol to 245° C. before boiling was observed. At this reaction temperature, nearly complete conversion was observed in 30 minutes; however, the appearance of a new unidentified by-product was observed by HPLC analysis. Without wishing to be bound by theory, it is possible that degradation of the product occurs at such high temperatures. It is notable that temperatures approaching 245° C. for ethanol in a microwave vial were ultimately not attainable in batch reactions due to the pressure limitations of the microwave system.

Using previous methods, ring opening of trisubstituted epoxides has also been a challenge in microwave-assisted aminolysis of epoxides. Thus, as expected, the microreactor gave similar results and poor conversions, even when a large excess of propylamine 14 was used to open I-phenylcyclohexene oxide 15 (Table 1, Trials 22 and 23). However, the use of the 500 psi backpressure regulator enabled a reaction temperature of 240° C. to be reached affording moderate conversions after 30 min residence times (Table 1, Entry 24). The use of 5 equiv of amine represents flowing almost a neat amine solution in one syringe; however, high reaction temperatures could still be maintained in the microreactor without flashing.

The opening of styrene oxide with aniline represents a unique aminolysis example as selectivity for the terminal over the benzylic position can be poor. Indeed, a batch microwave reaction in methanol led to aminolysis favoring the attack on the benzylic position 16 over the terminal position 17 in a 1.3:1 ratio. (FIG. 5) Switching to ethanol as the solvent in the microreactor, the reaction became unselective as the ratio of 16:17 changed to 1.1:1. Interestingly, increasing the temperature in the microreactor from 150° C. to 195° C. while keeping the backpressure constant gave a reversal in selectivity, albeit a slight one (1:1.2), with attack favored at the terminal end of the epoxide. The overall pressure of the system was maintained constant in this entry. Using the 500 psi backpressure regulator and temperatures of 245° C. in ethanol, selectivity for 17 was further enhanced to a ratio of 1:1.4. Similarly, a solvent switch to the bulkier and less polar isopropanol led to further increases in selectivity (1:1.8) for 17 at 225° C. and 250 psi in the microreactor.

Example 3

In this example, epoxide aminolysis reactions using a continuous flow microreactor was applied to the synthesis of metoprolol 19.

As shown in Table 2, the synthesis of metoprolol 19 centers around the aminolysis of the readily available epoxide 20 with isopropyl amine. The epoxide aminolysis is typically performed using multiple equivalents of isopropyl amine at reflux in a polar protic solvent, with reaction times ranging from 2 to 5 h. In examining batch microwave conditions, it was noted that the amount of 19 and bis-alkylation side product 21 was dependent on reactor headspace due to the low boiling point of isopropyl amine (Table 2, Entries 1 and 2). However, under microreactor conditions, loss of the volatile amine at high temperatures was not a concern. At 500 psi, temperatures up to 240° C. were achieved before flashing of ethanol was observed in the microreactor. Using only 1.2 equiv of isopropyl amine, almost full conversion and 72% yield of metoprolol were obtained with 1 min residence times (Table 2, Entry 5). Increasing the amount of isopropyl amine to 4 equiv did not hinder the ability to maintain the 240° C. reaction temperature, and excellent conversions (98%) were obtained in only 15 s (Table 2, Entry 8). The large excess of amine led to a significant decrease in the formation of 21 and a 91% yield of metoprolol was realized in extremely short reaction times. Under these conditions, a single 120 µL microreactor working under continuous flow operation is capable of delivering 7.0 g/h (61 kg/year) of metoprolol. Operating 17 microreactors in parallel could ultimately produce over 1 metric ton of this important drug per year.

TABLE 2

Results of metoprolol formation under microreactor-enabled conditions.

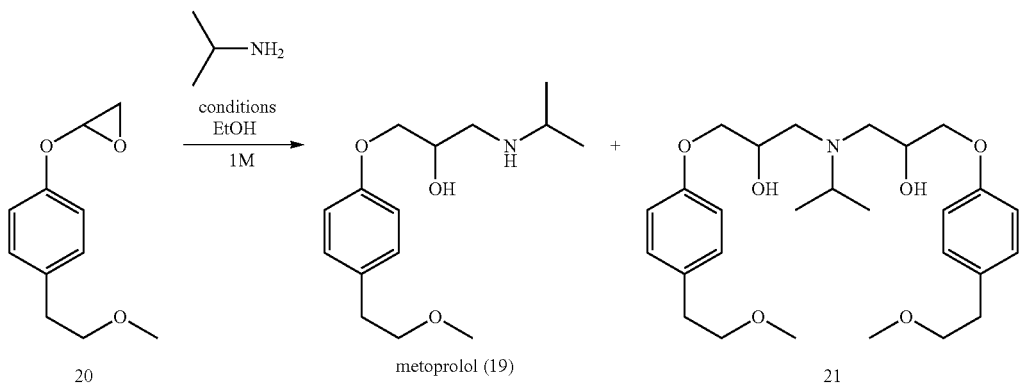

| Entry | Conditions (psi) | Amine Equiv | Temp (° C.) | Flow rate[a] (μL/min) | Time | Yield 19[b,c] (%) | Yield 21 (%) | conversion (%) |
|---|---|---|---|---|---|---|---|---|
| 1 | Batch μ_W[d] (~100) | 1.2 | 150 | — | 30 min | 65 | 31 | 100 |
| 2 | Batch μ_W[e] (~100) | 1.2 | 150 | — | 30 min | 69 | 28 | 100 |
| 3 | μ_reactor (500)[f] | 1.2 | 240 | 480 | 15 s | 61 | 14 | 76 |
| 4 | μ_reactor (500)[f] | 1.2 | 240 | 240 | 30 s | 69 | 21 | 92 |
| 5 | μ_reactor (500)[f] | 1.2 | 240 | 120 | 1 min | 72 | 24 | 99 |
| 6 | μ_reactor (500)[f] | 2.0 | 240 | 480 | 15 s | 80 | 8 | 89 |
| 7 | μ_reactor (500)[f] | 2.0 | 240 | 240 | 30 s | 86 | 12 | 99 |
| 8 | μ_reactor (500)[f] | 4.0 | 240 | 480 | 15 s | 91 | 6 | 98 |
| 9 | μ_reactor (500)[f] | 4.0 | 240 | 240 | 30 s | 91 | 6 | 100 |

[a] Combined flow rate of both reagents.
[b] All yields and conversions are calculated based on HPLC analysis with an internal standard.
[c] ~1% of the regioisomer can be isolated but was not quantified.
[d] 1 mL in a 5 mL vial.
[e] 2 mL in a 5 mL vial.
[f] Backpressure regulator.

Example 4

In this example, indacaterol 1, as shown in FIG. 1, a β-amino alcohol and novel β-adrenoceptor agonist, is studied. The reported current synthesis of 1 centers on the aminolysis of epoxide 2 with amine 3 to afford precursor 4 under a protracted reaction time. In addition, under the reaction conditions, the regioisomer 5 and a product of double alkylation (6) are also formed in significant quantities.

The adaptation of the indacaterol aminolysis to a microreactor system presented several unique challenges. First, the reported reaction time in diglyme at elevated temperatures was approximately 15 h, as shown in FIG. 1. Such lengthy residence times are generally not possible in a microreactor system due to difficulties in delivering the fluid in a stable (e.g., non-pulsating) manner at such low flow rates. Thus, initial studies described herein focused on decreasing reaction time in order to enable the use of a micro-scale flow system. Attempts to catalyze this reaction with a variety of known aminolysis promoters ultimately did not lead to reaction times that were amenable to microreactors. For example, attempts to catalyze the aminolysis with solid acid supports such as PMA-alumina, Amberlist-15, and ZnClO₄-alumina led to little or no product formation even after extended periods of time. Catalysis with lanthanide triflates such as Er(OTf)₃ and Yb(OTf)₃ ultimately led to shorter reaction times (e.g., approx. 5 h) but yielded large amounts of undesired by-products.

Figure 2:
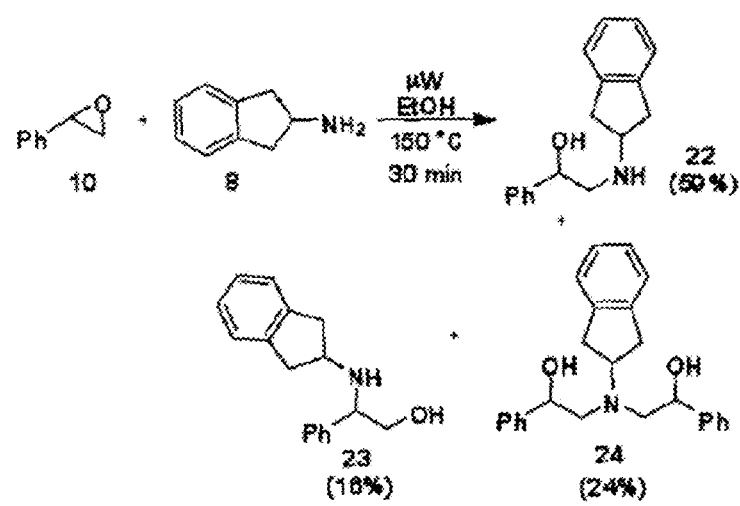
FIG. 2 illustrates the microwave aminolysis of styrene oxide with 2-aminoindan.

Fortuitously, heating at elevated temperatures in polar protic solvents such as ethanol resulted in reaction times that could be considered in microreactors (approx. 30 min) In order to better understand the effect of solvent on the aminolysis of a complicated example such as indacaterol, a similar model system, the aminolysis of styrene oxide with 2-aminoindan 8, was studied. This system was selected to provide a similar electronic and steric environment as the reaction between 2 and 3. Heating of this reaction mixture in the microwave at 150° C. for 30 min led to complete conversion, giving 59% of the desired product 22, as well as significant amounts of the regioisomer 23 and bisalkylation 24 side products. (FIG. 2) While this represented a significant decrease in reaction time, the overall selectivity for terminal over benzylic attack of the epoxide was decreased relative to the indacaterol reaction in diglyme.

While regioselectivity can sometimes be an issue in ethanol, it has also been reported that polar aprotic solvents can improve selectivity in aminolysis reactions at the expense of overall reaction rate. Thus, it was possible to take advantage of two unique aspects of microreactor technology. First, by altering temperature and flow rate, reaction conditions can be scanned quickly to find optimum conversion and product yield. Second, due to the absence of headspace, mixtures of polar protic and polar aprotic solvents can easily be employed without concern for the relative boiling point of each component. In this manner, a polar protic solvent may be considered as a potential promoter for the reaction.

Figure 5:
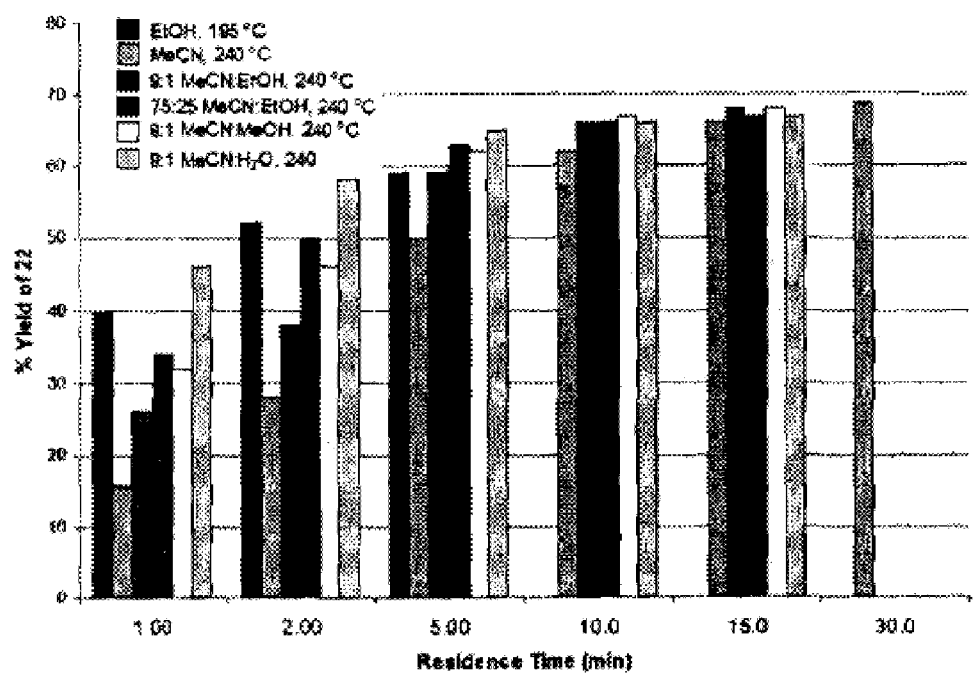
FIG. 5 shows a graph of reaction yield for aminolysis of styrene oxide with 2-aminoindan 8, at different residence times and using different polar protic solvents.

FIG. 5 shows a graph of reaction yield for aminolysis of styrene oxide with 2-aminoindan 8, at different residence times and using different polar protic solvents. Using ethanol as a baseline, the microreactor aminolysis was nearly complete in 5 min at 195° C. to afford 59% of 22 along with 14% of the regioisomer 23. Switching to acetonitrile as the solvent and operating with a 250 psi backpressure regulator, temperatures up to 240° C. were easily obtained before flashing of the solution was observed in the microreactor. Even at this increased temperature, product yields were markedly lower when compared to those in ethanol at similar residence times. (FIG. 4) However, a 30 min residence time resulted in completion of the aminolysis and up to 69% of 22 was obtained, as quantified by HPLC analysis. The increase in overall product yield was derived mainly from the improved regioselectivity of the reaction, as attack at the terminal position of the epoxide over the benzylic position is favored in a 7.7:1 ratio compared to 4.2:1 in ethanol. Incorporation of a 9:1 mixture of acetonitrile to ethanol in the microreactor efficiently accelerated the reaction to where conversions of 99% were achieved in only 15 min. Yields of 22 were maintained at a high level (68%) and the selectivity ratio remained at 7.5:1. Changing the solvent system to either 75:25 acetonitrile/ethanol or 9:1 acetonitrile/methanol also gave improved conversions at comparable residence times. Finally, using a ratio of 9:1 acetonitrile/water, conversions at similar time intervals surpassed those obtained in pure ethanol at 195° C. and nearly complete aminolysis was observed at a 10 min residence time with 66% yield of 22. Regioselectivity was only slightly altered under these conditions (5.6:1) enabling us to consider using water as promoter in the aminolysis reaction.

Another obstacle to performing the indacaterol aminolysis in the microreactor was low solubility of the starting epoxide 2 in commonly used solvents. The quinolinone structure provided a highly crystalline material that had a limited solubility (<0.1 M) in most organic solvents, including ethanol and acetonitrile. Formation of solids in the microreactor ultimately would clog the inlets and prevent flow. To solve this problem, a solvent screen was conducted. N-Methylpyrrolidone (NMP) emerged as a likely reaction solvent, as 2 exhibited moderate solubility (~0.5 M), and the dielectric constant of NMP is similar to that of acetonitrile. Operationally, we would also be able to keep the concentration of the reaction high by pre-mixing the amine and epoxide in order to flow the mixture from one syringe. This technique avoids further dilution of the reaction when the two components are introduced separately, and thus enables higher overall conversion.

An additional issue to address in the formation of 4 was the thermal stability of the product as a free base. According to previous studies, compound 4 is unstable in organic solvents. In this study, significant decomposition was observed when the indacaterol precursor 4 was heated to temperatures above 200° C. Considering these issues, a solution of 2 and 3 was prepared in NMP and 10% water was added as a promoter for the aminolysis reaction. Initially, a 0.4 M solution was pumped through the microreactor at 185° C. and varying flow rates in order to establish reaction parameters. Excellent conversion (97%) was obtained at 185° C. in only 15 min with 68% of the desired indacaterol precursor 4 produced (Table 3, Entry 4). Yields and selectivities observed under microreactor conditions mirrored those obtained by heating in diglyme for a period 60 times longer. Small amounts of 2 were found to have crystallized out in the syringe after 12 h at room temperature but did not lead to crystallization and clogging in the microreactor. At a slightly decreased concentration of the starting solution (0.38 M), 2 was completely soluble, and multiple repetitions of the aminolysis reaction under the same conditions led to yields of 4 between 6870% (Table 3, Entries 5 and 6). Decreasing the temperature to 165° C. reduced the degree of thermal decomposition of 4 and slightly increased yields were obtained at the expense of longer reaction times (Table 3, Entry 7). Similarly, increasing the temperature to 200° C. led to better conversion at shorter times at the expense of overall product yield (Table 3, Entry 8). Under the best observed conditions in this example (Table 3, Entry 5), 1.5 g/d (0.5 kg/year) of the indacaterol precursor 4 could be obtained from a single 120 μL microreactor.

TABLE 3

Results of Indacaterol precursor formation under microreactor-enabled conditions.

| Entry | Conditions (psi)[a] | Solvent | Conc[b] | Equiv 2 | Temp (° C.) | Flowrate (μL/min) | Time | Yield 4[c] (%) | Yield 5 (%) | Yield 6 (%) | conv (%) |
|---|---|---|---|---|---|---|---|---|---|---|---|
| 1 | Novartis (Batch) | Diglyme | 1M | 1.2 | 110 | — | 15 h | 68.7 | 7.8 | 12.4 | — |
| 2 | Oil Bath (Batch) | Diglyme | 1M | 1.2 | 110 | — | 15 h | 68.4 | 6.4 | 10.4 | 95.4 |
| 3 | Batch (μW) | 9:1 NMP:H$_2$O | 0.5M | 1.2 | 185 | 8 | 15 min | 68.1 | 6.3 | 7.7 | 95.4 |
| 4 | μreactor (250) | 9:1 NMP:H$_2$O | 0.4M | 1.2 | 185 | 8 | 15 min | 67.8 | 8.6 | 9 | 97 |
| 5 | μreactor (250) | 9:1 NMP:H$_2$O | 0.38M | 1.2 | 185 | 8 | 15 min | 70 | 8 | 7.1 | 92.8 |
| 6 | μreactor (250) | 9:1 NMP:H$_2$O | 0.38M | 1.2 | 185 | 8 | 15 min | 68.3 | 8.2 | 7.5 | 95.1 |
| 7 | μreactor (250) | 9:1 NMP:H$_2$O | 0.38M | 1.2 | 165 | 4 | 30 min | 72.1 | 8.6 | 7.9 | 92.4 |
| 8 | μreactor (250) | 11:1 NMP:H$_2$O | 0.37M | 1.2 | 200 | 12 | 10 min | 60.7 | 6.8 | 6.4 | 92.3 |

[a]Pressure of back pressure regulator.
[b]Concentration of epoxide in reaction vessel or in one syringe pre-mixed with the amine.
[c]All yields are conversions are based on HPLC with an internal standard.

In contrast, simple heating of the reaction in ethanol at 150° C. under microwave irradiation or in an oil bath resulted in complete conversion within 35 min with moderate (~60%) product formation. Given the demonstrated effectiveness of microreactors in achieving high temperatures and pressures in a continuous flow manner, a study of epoxide aminolysis reactions was pursued using this technology. These results as well as the application of this technique toward the synthesis of pharmaceutically relevant compounds indacaterol and metoprolol are presented herein.

Example 5

Materials and Methods. All solvents, epoxides, and amines were purchased from commercial sources and used without further purification, unless otherwise noted. The indacaterol substrates 2 and 3 were prepared according to literature procedures. The epoxide 20 for metoprolol was synthesized from the corresponding phenol and epichlorohydrin according to published reports.

All aminolysis reactions were initially performed as 1 M solutions in ethanol using a Biotage Initiator single cavity microwave reactor under normal absorption and in 0.5-2 mL sealed vials (5 mL total volume). The products were then separated either with preparative TLC on precoated silica gel 60 F254 glass sheets or by chromatography on Silicycle silica gel (230-400 mesh), eluting with hexane/ethyl acetate or dichloromethane/methanol. All components were analyzed by $^1$H NMR spectroscopy using a Bruker-Avance 400 MHz spectrometer and compared to known literature compounds when available. HPLC quantitative analysis was performed Ion an Agilent 1200 Series LC/MS using either an Eclipse XDB-CI8 or a Zorbax Eclipse Plus CI8 reverse phase column, a methanol/water mobile phase, and a 254 or 210 nm wavelength detector.

Yields were calculated based on normalization of response factors using naphthalene as an internal standard. GC quantitative analysis was performed on an Agilent 7890A GC system. Yields were calculated based on normalization of response factors using dodecane as an internal standard.

Microreactor Fabrication and Set Up. The microreactor was fabricated using standard silicon micromachining techniques. Channel layout was defined by photolithography and realized by deep reactive ion etching (DRIE) of a silicon wafer (15 cm diameter; 0.65 mm thickness) to a depth of 0.40 μm (micron). A silicon nitride layer (500 nm) was grown on the silicon surface, and the entire device was capped and sealed by anodically bonding a Pyrex wafer (1.0 mm thickness).

The inlet and outlet section of the reactor was compressed in a custom microfluidic chuck (holder connecting the microreactor to heat and an conventional fluid handling elements) machined out of aluminum. Kalrez O-rings (Z1028 FFKM, size 005, Marco Rubber) were used to seal the fluidic connections. The chuck was machined with 10-32 ports, and polyetheretherketone (PEEK) fittings were used (Upchurch Nanotight® headless fittings, F-333N), connecting to 1/16" OD, 0.020" ID PEEK tubing. The third inlet, which remained unused, was capped with a PEEK plug (Upchurch P550). Inlet tubing was connected to 8-mL high-pressure stainless steel syringes (702267, Harvard Apparatus), which were independently driven by two syringe pumps (PHD 2200, Harvard Apparatus). The outlet tubing was connected to a backpressure regulator, either 250 psi (U-608, Upchurch) or 500 psi (U-609, Upchurch).

The fluidic compression chuck was cooled by house cooling water via two channels 3/16" in diameter drilled through the chuck. The reaction zone of the reactor was compressed between a 3/8" thick piece of borosilicate glass and a 1/16" thick piece of graphite, which was in direct contact with a custom-machined aluminum heating chuck. The heating chuck was drilled with two holes for insertion of 1/8" diameter cartridge heaters (35 W, 120 V, CSS-01235/120V, Omega) and a 1-mm-diameter hole for a wire thermocouple (K-type, SC-GG-K-30-36, Omega), placed 0.5 mm beneath the chuck surface. The thermocouple provided data to a PID controller (CN742, Omega), which controlled the cartridge heaters via a solid-state relay (SSRL240DC10, Omega).

General Batch Microwave Protocol. The desired epoxide (1.0 mmol), amine (1.2 mmol), and internal standard (10-20 mol %) were combined in a 0.5-2 mL (5 mL total volume) microwave vial and diluted to 1 mL with ethanol. The vial was then sealed, placed in the microwave cavity, and irradiated at normal absorption for 30 min at 150° C. Samples for quantitative analysis were then taken before the reaction mixture was concentrated and the crude products were purified by chromatography on silica gel or preparative TLC. The desired products were analyzed by $^1$H and $^{13}$C NMR spectroscopy as well as HRMS and were compared to known literature compounds when available.

Microreactor Protocols for General and Metoprolol Epoxide Aminolysis. A solution of the desired epoxides (10 mmol) and naphthalene (internal standard, 10-20 mol %) was diluted to 5 mL with ethanol and placed in an 8 mL high-pressure stainless steel syringe. A solution of the amine (12 mmol for 1.2 equivalents) was diluted to 5 mL with ethanol and placed in a separate 8 mL syringe before being connected to the microreactor. The reagent streams were pumped through the microreactor (250 or 500 psi backpressure regulators were used) at identical flow rates, and reaction times and temperatures were varied. In general, five microreactor volumes (5×120 pL) were allowed to pass through the outlet after each change in conditions in order to achieve steady state before samples were taken for quantitative analysis.

Microreactor Protocol for Formation of Indacaterol Precursor 4. The epoxide 2 (234.2 mg, 0.79 mmol) and naphthalene (internal standard, 15.7 mg, 0.120 mmol) were dissolved in NMP (1.8 mL) and the suspension was heated gently to affect dissolution of the solid. After cooling, H$_2$O (200 mL) and amine 3 (181.7 mg, 0.96 mmol) were added to the mixture and stirred before being placed in an 8 mL high-pressure stainless steel syringe and connected to the microreactor. The reaction mixture was pumped through the microreactor (250 psi backpressure regulator) at desired flow rates and temperatures. In general, five microreactor volumes (5×120 μL) were allowed to pass through the outlet before 5 μL samples were taken for quantitative analysis.

What is claimed:

1. A method for synthesizing an amino alcohol, comprising:
   providing a continuous flow microreactor comprising a microchannel, a first inlet in fluid communication with a source of an epoxide species and the microchannel, and a second inlet in fluid communication with a source of an amine species and the microchannel;
   flowing a fluid sample comprising the epoxide species and the amine species into the microchannel; and
   reacting, in the microchannel, the epoxide species and the amine species to form an amino alcohol.

2. A method as in claim 1, comprising:
   reacting, in the microchannel, the epoxide species and the amine species for a reaction time of about 15 hours or less, to produce an amino alcohol in a yield of at least 50%.

3. A method as in claim 1, comprising:
   reacting, in the microchannel, the epoxide species and the amine species in the presence of water and at least one organic solvent to produce an amino alcohol in a yield of at least 50%.

4. A method as in claim 1, wherein the amino alcohol is a β-amino alcohol.

5. A method as in claim 1, wherein the act of reacting is performed in the presence of at least one organic solvent.

6. A method as in claim 5, wherein the organic solvent is an alcohol, naphthalene, or N-methyl pyrrolidone.

7. A method as in claim 5, wherein the organic solvent is N-methyl pyrrolidone.

8. A method as in claim 1, wherein the act of reacting is performed in the presence of N-methyl pyrrolidone and water.

9. A method as in claim 1, wherein the act of reacting is performed in the absence of a Lewis acid or a strong base.

10. A method as in claim 1, wherein the reaction time is about 10 hours or less.

11. A method as in claim 1, wherein the reaction time is about 5 hours or less.

12. A method as in claim 1, wherein the reaction time is about 3 hours or less.

13. A method as in claim 1, wherein the reaction time is about 1 hour or less.

14. A method as in claim 1, wherein the reaction time is about 30 minutes to about 1 hour.

15. A method as in claim 1, wherein the amino alcohol is produced in a yield of at least 60%.

16. A method as in claim 1, wherein the amino alcohol is produced in a yield of at least 70%.

17. A method as in claim 1, wherein the amino alcohol is produced in a yield of at least 80%.

18. A method as in claim 1, wherein the amino alcohol is produced in a yield of at least 90%.

19. A method as in claim 1, wherein the amino alcohol is produced in a yield of at least 95%.

20. A method as in claim 1, wherein the amino alcohol is produced in a yield of at least 97%.

21. A method as in claim 1, wherein the amino alcohol is produced in a yield of at least 99%.

22. A method as in claim 1, wherein the act of reacting is performed at a temperature of at least 80° C.

23. A method as in claim 1, wherein the amine species has the formula, $NR^1R^2R^3$, wherein $R^1$, $R^2$, and $R^3$ can be the same or different and are hydrogen, alkyl, heteroalkyl, aryl, heteroaryl, or a carbonyl group, wherein any of $R^1$, $R^2$, and $R^3$ may be substituted or any of $R^1$, $R^2$, and $R^3$ may be joined to form a ring, wherein the ring may be substituted.

24. A method as in claim 1, wherein the amine species has the formula, $NH_2R^3$, wherein $R^3$ is hydrogen, alkyl, heteroalkyl, aryl, heteroaryl, or a carbonyl group, any of which may be substituted.

25. A method as in claim 1, wherein the epoxide species has the formula,

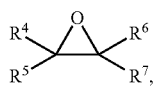

wherein:

$R^4$, $R^5$, $R^6$, and $R^7$ can be the same or different and are hydrogen, alkyl, heteroalkyl, aryl, heteroaryl, or a carbonyl group, wherein any of $R^4$, $R^5$, $R^6$, and $R^7$ may be substituted or any of $R^4$, $R^5$, $R^6$, and $R^7$ may be joined to form a ring, wherein the ring may be substituted.

26. A method as in claim 25, wherein $R^4$, $R^5$, and $R^6$ are each hydrogen.

27. A method as in claim 1, wherein the method comprises the reaction represented by the following,

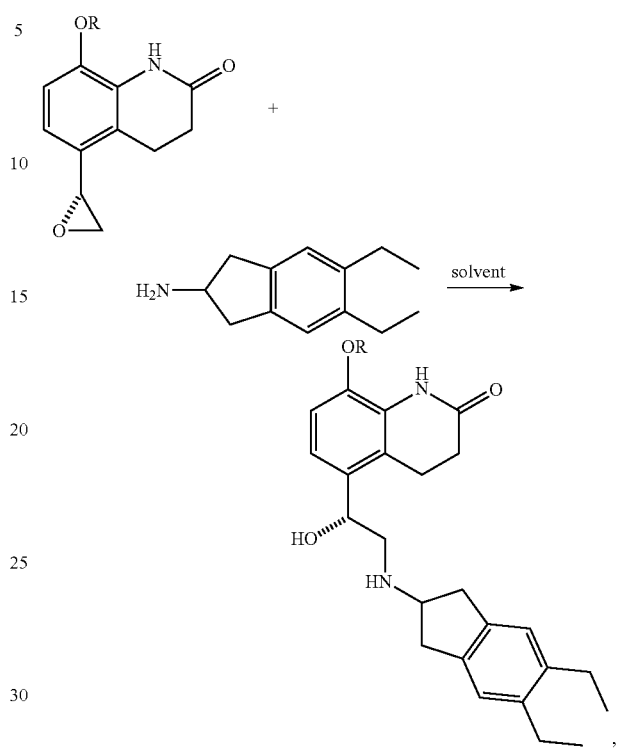

wherein R is a protecting group.

28. A method as in claim 1, wherein the method comprises the reaction represented by the following,

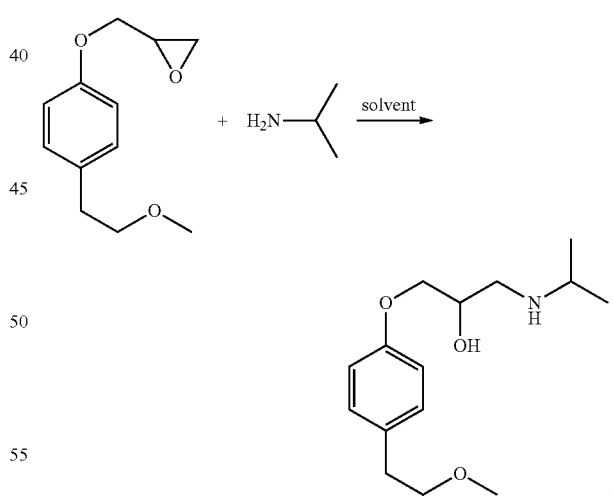

* * * * *